US012810133B2

(12) United States Patent
Choi et al.

(10) Patent No.: US 12,810,133 B2
(45) Date of Patent: Nov. 24, 2026

(54) GAS RESPONSIVE NEURON MODULE FOR IMPLEMENTING NEUROMORPHIC ELECTRONIC NOSE, AND GAS SENSING SYSTEM USING IT

(71) Applicant: Korea Advanced Institute of Science and Technology, Daejeon (KR)

(72) Inventors: Yang-Kyu Choi, Daejeon (KR); Inkyu Park, Daejeon (KR); Joon-Kyu Han, Daejeon (KR); Mingu Kang, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 948 days.

(21) Appl. No.: 17/976,945

(22) Filed: Oct. 31, 2022

(65) Prior Publication Data

US 2023/0153598 A1 May 18, 2023

(30) Foreign Application Priority Data

Nov. 1, 2021 (KR) ........................ 10-2021-0147586

(51) Int. Cl.
*G06N 3/065* (2023.01)
*A61B 5/145* (2006.01)

(52) U.S. Cl.
CPC ............. *G06N 3/065* (2023.01); *A61B 5/145* (2013.01)

(58) Field of Classification Search
CPC ........................................................ G06N 3/06
See application file for complete search history.

(56) References Cited

U.S. PATENT DOCUMENTS

| | | | | |
|---|---|---|---|---|
| 5,864,255 | A * | 1/1999 | Kwok | G06G 7/164 327/120 |
| 10,553,683 | B2 * | 2/2020 | Han | H10D 89/213 |
| 2006/0199271 | A1 * | 9/2006 | Lian | G05D 23/1919 436/155 |
| 2007/0252204 | A1 * | 11/2007 | Wei | H10D 64/259 257/E21.336 |
| 2010/0019299 | A1 * | 1/2010 | Bae | H10D 86/201 257/296 |
| 2020/0033309 | A1 * | 1/2020 | Yuan | G01N 33/0016 |
| 2021/0063372 | A1 * | 3/2021 | Mannari | G01N 33/0073 |
| 2021/0249473 | A1 * | 8/2021 | Sekar | H10D 86/215 |
| 2021/0296157 | A1 * | 9/2021 | Or-Bach | H10D 88/00 |

* cited by examiner

*Primary Examiner* — Jeff W Natalini
*Assistant Examiner* — Jacob Raul Marin
(74) *Attorney, Agent, or Firm* — Adams & Reese LLP

(57) ABSTRACT

The present disclosure relates to a gas-responsive neuron module including a resistive gas sensor for sensing gaseous molecules and converting the sensed gaseous molecules into an electrical signal, and a single transistor neuron composed of a source, a drain, and a gate, and a gas sensing system for sensing gas including the same, for implementing a high-integration and low-power neuromorphic electronic nose.

17 Claims, 18 Drawing Sheets

100

GAS RESPONSIVE NEURON MODULE FOR IMPLEMENTING NEUROMORPHIC ELECTRONIC NOSE, AND GAS SENSING SYSTEM USING IT

CROSS-REFERENCE TO RELATED APPLICATIONS

A claim for priority under 35 U.S.C. § 119 is made to Korean Patent Application No. 10-2021-0147586 filed on Nov. 1, 2021, in the Korean Intellectual Property Office, the entire contents of which are hereby incorporated by reference.

BACKGROUND

Embodiments of the present disclosure described herein relate to a gas-responsive neuron module for implementing a high-integration and low-power neuromorphic electronic nose, and a gas sensing system including the same.

With a development of Internet of Things (IoT), a demand for portable and personalized gas monitoring devices is increasing. In particular, a personal mobile gas sensor is used in a variety of applications, such as air pollution-related indoor/outdoor air quality monitoring, early diagnosis of a respiratory-related disease, and food/beverage quality monitoring and identification. In addition, the mobile gas sensor is widely used in an industrial field to increase production yield and ensure safety of workers from a toxic gas. In particular, an electronic nose (E-nose), which imitates a biological olfactory system, is attracting great attention from the research and industrial world by accurately identifying a gas using a sensor array and an artificial intelligence system. An existing electronic nose is composed of the sensor array, an electronic circuit for signal preprocessing such as an analog-digital converter, and a von Neumann-based computer for pattern recognition. However, the conversion circuit required when data is transmitted from the sensor to a processor takes up a large hardware area, and a bottleneck phenomenon occurs during a conversion process, resulting in additional power consumption. In addition, because the von Neumann-based computer for implementing the pattern recognition is composed of a central processing unit, a graphic processing unit, and a memory, not only hardware with a large area is required, but also a lot of energy is consumed based on repetitive data movement between the processing unit and the memory. Therefore, it is difficult to implement small-sized hardware with low power consumption in an existing scheme, and there are limitations in application to a portable gas monitoring device for the Internet of Things.

On the other hand, it is known that the biological olfactory system may minimize the power consumption by implementing spike-based parallel operation. To mimic such biological olfactory system and overcome the limitations of the existing von Neumann scheme, a neuromorphic-based spiking neural network (SNN) is in the limelight. However, because a signal collected from a gas environment must be converted into a form of a spike to apply the SNN to a gas sensing system, a general gas sensor is not able to be used. Therefore, it is required to develop a neuron element or a neuron module capable of sensing the gas and generating the spike at the same time.

SUMMARY

Embodiments of the present disclosure present a gas-responsive neuron module for implementing a neuromorphic-based electronic nose, and a gas sensing system including the same.

Embodiments of the present disclosure implement a high-integration and low-power electronic nose for a portable gas monitoring device for Internet of Things by reducing a hardware area and energy consumption of the electronic nose because a conversion circuit for signal transmission between a sensor array and a processor and a von Neumann-based computer for pattern recognition of an existing electronic nose are able to be removed.

However, technical problems to be solved by the present disclosure are not limited to the above problems, and may be variously extended within a range that does not deviate from the technical spirit and scope of the present disclosure.

According to an embodiment, a gas-responsive neuron module includes a resistive gas sensor for sensing gaseous molecules and converting the sensed gaseous molecules into an electrical signal, and a single transistor neuron composed of a source, a drain, and a gate.

The resistive gas sensor may be formed as one of a semiconducting metal oxide (SMO) gas sensor, a carbon nanotube (CNT)-based gas sensor, and a polymer-based gas sensor.

The SMO gas sensor may be formed of one of tin oxide ($SnO_2$), tungsten oxide ($WO_3$), zinc oxide (ZnO), indium oxide ($In_2O_3$), titanium oxide ($TiO_2$), copper oxide (CuO), and nickel oxide (NiO).

The resistive gas sensor may be simultaneously integrated with a heater or a photoactive platform for increasing a temperature to improve responsiveness of the SMO gas sensor.

The carbon nanotube-based gas sensor may be formed as a single-walled carbon nanotube or a multi-walled carbon nanotube, and the polymer-based gas sensor may be formed of one of polypyrrole, polyaniline, polythiophene, polyacetylene, and a conductive polymer.

The single transistor neuron may include a semiconductor substrate, a hole barrier material layer formed on top of the semiconductor substrate, a floating body layer formed on top of the hole barrier material layer, the source and the drain formed on left and right sides or on top of and beneath the floating body layer, a gate insulating film formed on top of the floating body layer, and the gate formed on top of the gate insulating film.

The gate may serve as a biological interneuron by performing an inhibition function, and the drain may serve as a biological mitral cell by performing a function of outputting a spike signal.

The hole barrier material layer may be formed of one of buried oxide, a buried n-well in a case of being a p-type body, a buried p-well in a case of being an n-type body, buried SiC, and buried SiGe.

Holes generated by impact ionization may be accumulated in the floating body layer, and the floating body layer is formed of one of silicon, germanium, silicon germanium, and a group 3-5 compound semiconductor.

The floating body layer may be formed in a horizontal direction or a vertical direction on the semiconductor substrate, and the single transistor neuron may represent a horizontal transistor structure when the floating body layer is formed in the horizontal direction, and the single transistor neuron may represent a vertical transistor structure when the floating body layer is formed in the vertical direction.

The floating body layer may include a lower substrate, and the lower substrate may be operable as a back-gate.

The source and the drain may be formed on the left and right sides of the floating body layer in a case of a horizontal transistor, formed on top of and beneath the floating body layer in a case of a vertical transistor, and formed of one of n-type silicon, p-type silicon, and metal silicide.

The source and the drain formed of n-type silicon or p-type silicon may be formed via one of diffusion, solid-phase diffusion, epitaxial growth and selective epitaxial growth, ion implantation, and subsequent heat treatment.

The gate may represent a gate-all-around (GAA) structure of surrounding an entirety of the floating body layer.

The gate may represent a multiple-gate structure of a double-gate, a tri-gate, and an omega-gate.

The neuron module may apply an appropriate voltage to the gate to inhibit spiking for enabling gas identification.

The neuron module may include the resistive gas sensor and the single transistor neuron manufactured on different substrates and connected to each other by wire bonding, or the resistive gas sensor and the single transistor neuron manufactured on the same substrate and connected to each other by interconnect metal.

According to an embodiment, a gas-responsive neuron module includes a resistive gas sensor for sensing gaseous molecules and converting the sensed gaseous molecules into an electrical signal, and a single transistor neuron composed of a source, a drain, and a gate, and the single transistor neuron includes a semiconductor substrate, a hole barrier material layer formed on top of the semiconductor substrate, a floating body layer formed on top of the hole barrier material layer, the source and the drain formed on left and right sides or on top of and beneath the floating body layer, a gate insulating film formed on top of the floating body layer; and the gate formed on top of the gate insulating film.

According to an embodiment, a gas sensing system for sensing gas includes a neuron module including a resistive gas sensor for sensing gaseous molecules and converting the sensed gaseous molecules into an electrical signal, and a single transistor neuron including a source, a drain, and a gate for implementing a high-integration and low-power neuromorphic electronic nose.

The gas sensing system may include one or more additional components of a synaptic element, a resistor, a capacitor, and a transistor in addition to the gas-responsive neuron module.

According to an embodiment, a gas-responsive neuron module includes a resistive gas sensor for sensing gaseous molecules and converting the sensed gaseous molecules into an electrical signal, and a single transistor neuron composed of a source, a drain, and a gate, the single transistor neuron includes a semiconductor substrate, a hole barrier material layer formed on top of the semiconductor substrate, a floating body layer formed on top of the hole barrier material layer, the source and the drain formed on left and right sides or on top of and beneath the floating body layer, a gate insulating film formed on top of the floating body layer; and the gate formed on top of the gate insulating film, the gate serves as a biological interneuron by performing an inhibition function of spiking to enable gas identification with improved signal contrast difference, and the drain serves as a biological mitral cell by performing a function of outputting a spike signal.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
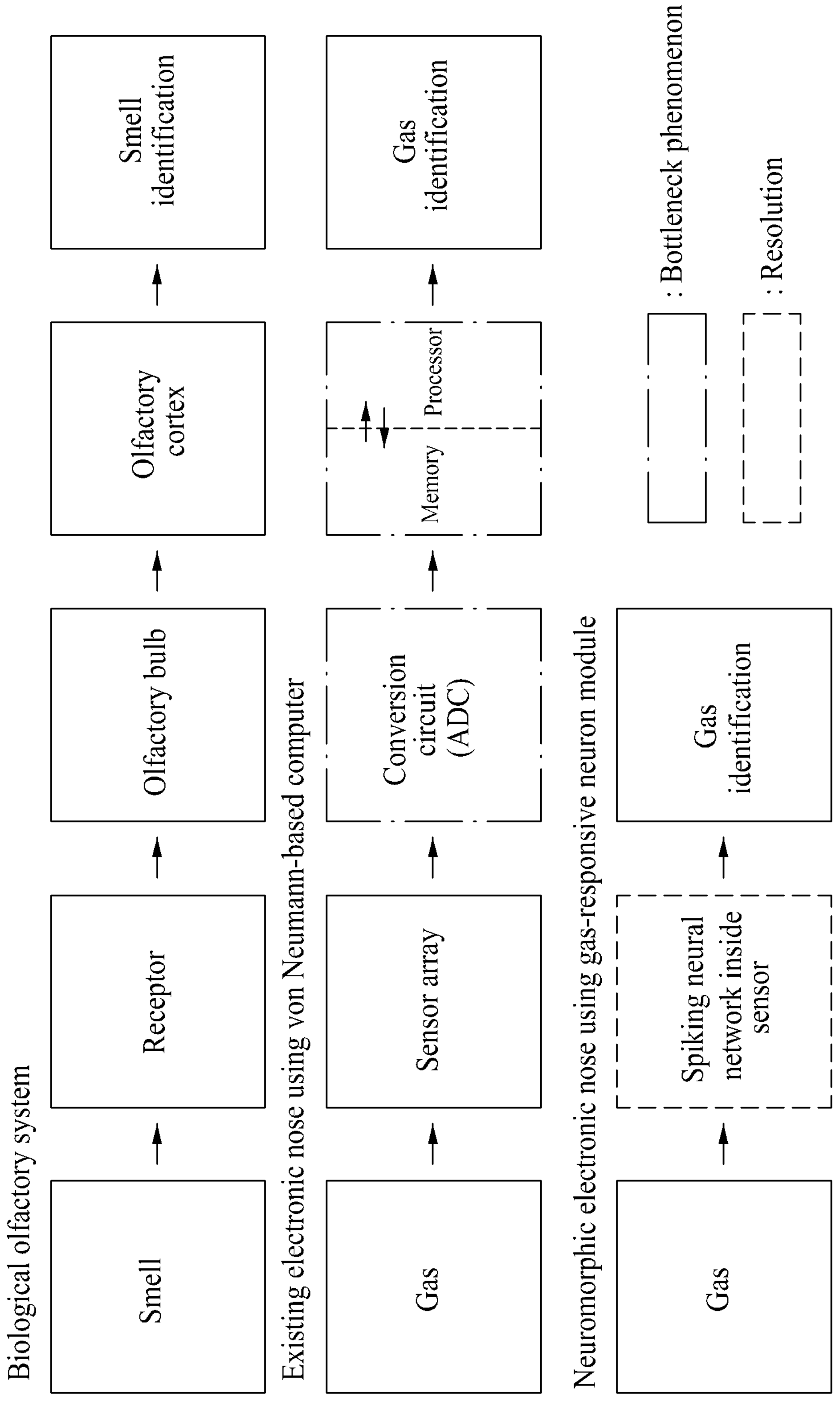
FIG. 1 is a view for comparing a biological olfactory system, an existing electronic nose using a von Neumann-based computer, and a neuromorphic electronic nose using a neuron module, which uses a gas-responsive neuron module according to an embodiment of the present disclosure, with each other.

Advantages and features of the present disclosure, and a method of achieving them will become apparent with reference to embodiments described below in detail together with the accompanying drawings. However, the present disclosure is not limited to the embodiments disclosed below, but may be implemented in various different forms. The present embodiments are provided to merely complete the disclosure of the present disclosure, and to merely fully inform those skilled in the art of the present disclosure of the scope of the present disclosure. The present disclosure is only defined by the scope of the claims.

The terminology used herein is for the purpose of describing the embodiments only and is not intended to limit the present disclosure. As used herein, the singular forms "a" and "an" are intended to include the plural forms as well, unless the context clearly indicates otherwise. The terms "comprises", "comprising", "includes", and "including" when used in this specification, specify the presence of the stated features, integers, operations, elements, and/or components, but do not preclude the presence or addition of one or greater other features, integers, operations, elements, components, and/or portions thereof.

Unless otherwise defined, all terms including technical and scientific terms used herein have the same meaning as commonly understood by one of ordinary skill in the art to which the present disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, preferred embodiments of the present disclosure will be described in more detail with reference to the accompanying drawings. The same reference numerals are used for the same components in the drawings, and repeated descriptions of the same components are omitted.

FIG. 1 is a view for comparing a biological olfactory system, an existing electronic nose using a von Neumann-based computer, and a neuromorphic electronic nose using a neuron module, which uses a gas-responsive neuron module according to an embodiment of the present disclosure, with each other.

Referring to FIG. 1, in the biological olfactory system, a receptor senses gaseous molecules, converts the gaseous molecules into an electrical signal, and then transmits the signal to an olfactory bulb. After the signal preprocessed in the olfactory bulb is transmitted to an olfactory cortex, it is possible to determine what kind of smell it is via a neural network.

The electronic nose may discriminate gas with high accuracy by imitating such biological olfactory system. In the existing electronic nose using the von Neumann-based computer, a sensor array senses the gas and then transfers an output signal to an electronic circuit for signal preprocessing such as an analog-digital converter. Thereafter, the gas is determined via pattern recognition in the von Neumann-based computer. However, a conversion circuit required when data is transmitted from the sensor to a processor takes up a large hardware area, and a bottleneck phenomenon occurs during a conversion process, resulting in additional power consumption. In addition, because the von Neumann-based computer for implementing the pattern recognition is composed of a central processing unit, a graphic processing unit, and a memory, not only hardware with a large area is required, but also a lot of energy is consumed based on repetitive data movement between the processing unit and the memory. Therefore, it is difficult to implement small-sized hardware with low power consumption in an existing scheme, and there are limitations in application to a portable gas monitoring device for the Internet of Things (IoT). On the other hand, it is known that the biological olfactory system may minimize the power consumption by implementing spike-based parallel operation.

The neuromorphic electronic nose using the gas-responsive neuron module proposed in the present disclosure mimics various olfactory neurons, so that the pattern recognition may be performed in a spiking neural network (SNN) inside the sensor, and the bottleneck phenomenon of the existing electronic nose using the von Neumann-based computer may be eliminated.

Figure 2:
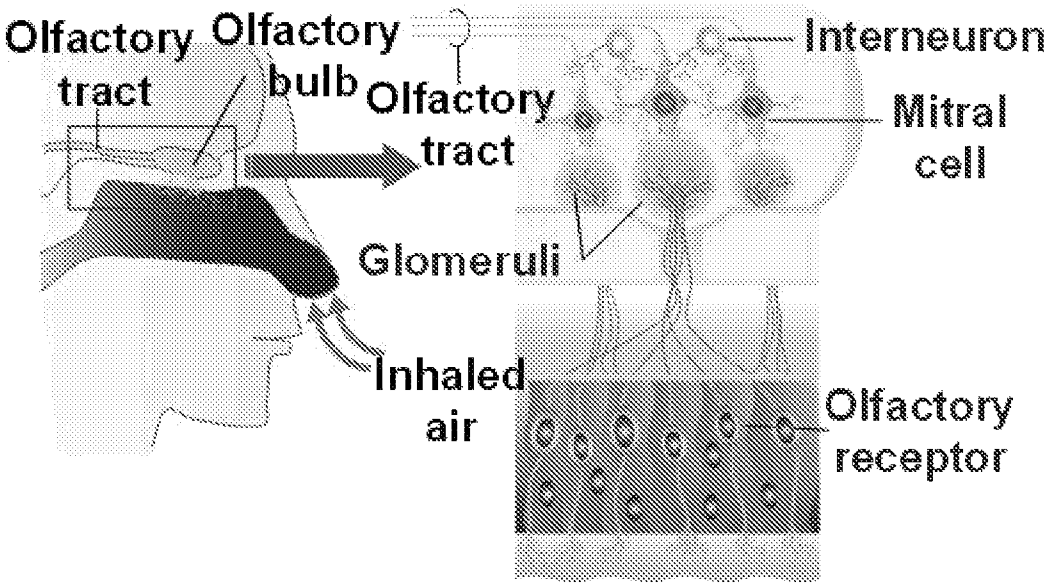
FIG. 2 shows a structure of a biological olfactory system composed of various olfactory neurons according to an embodiment of the present disclosure.
Figure 3A:
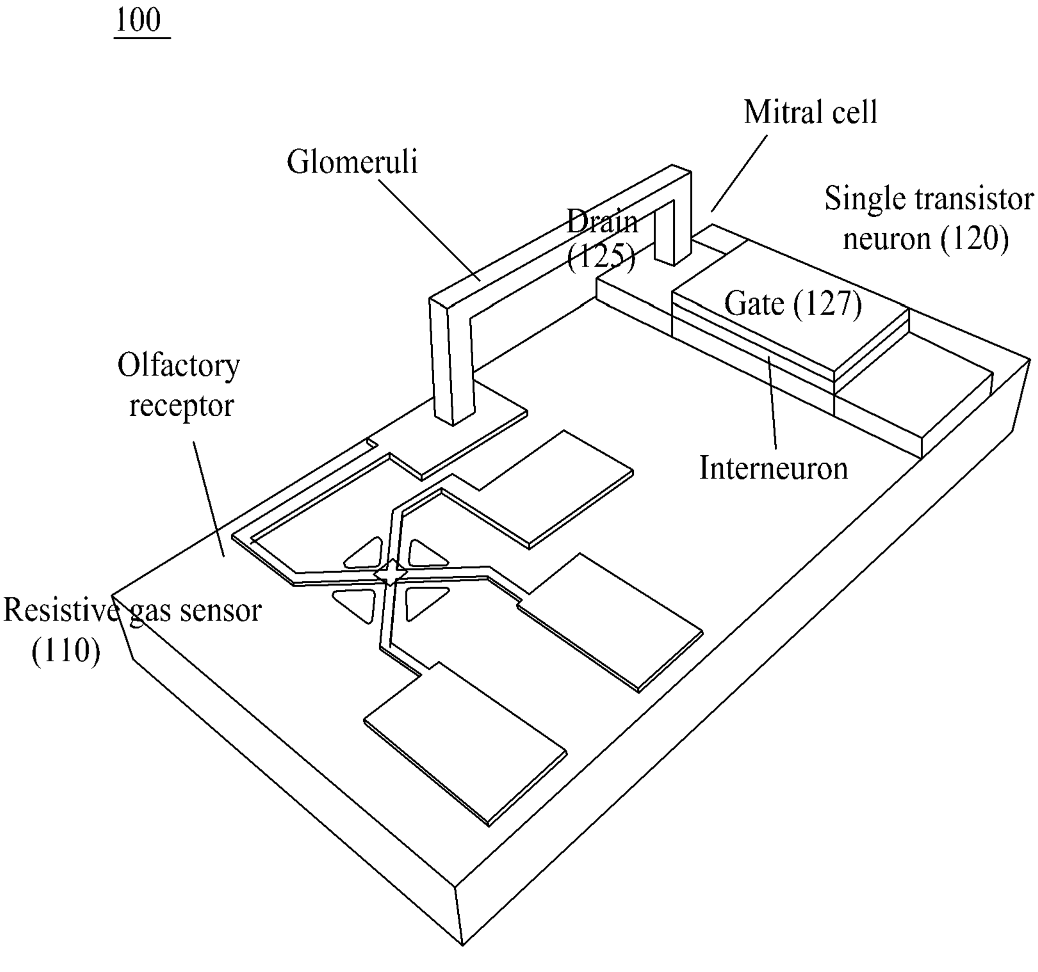
FIG. 3A shows a structure of a gas-responsive neuron module, mimicking olfactory neurons according to an embodiment of the present disclosure.
Figure 3B:
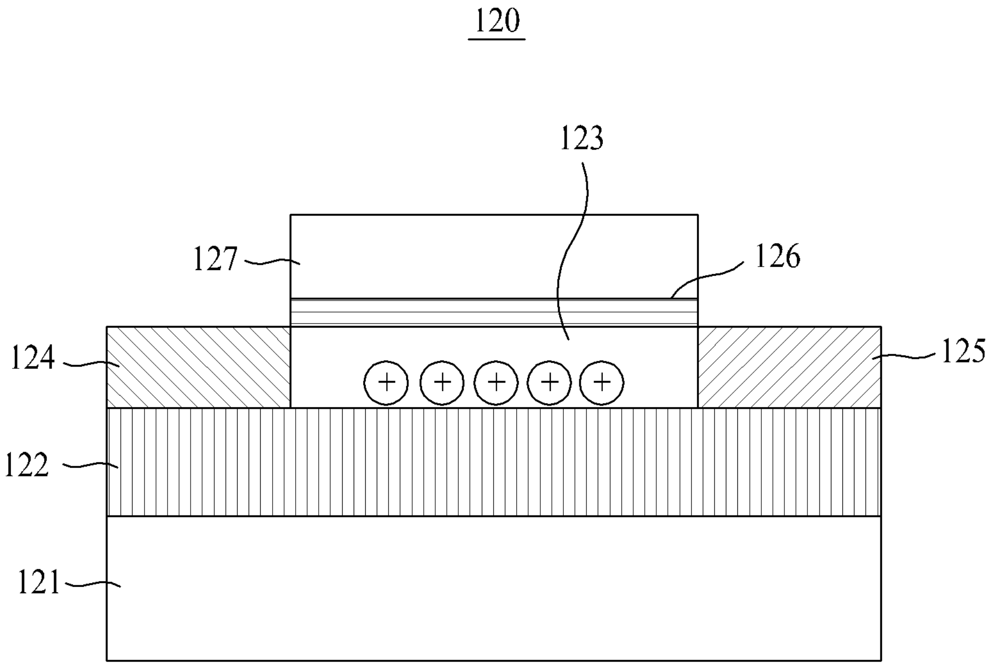
FIG. 3B shows a cross-sectional view of a single transistor neuron formed in a neuron module according to an embodiment of the present disclosure.

FIG. 2 shows a structure of a biological olfactory system composed of various olfactory neurons according to an embodiment of the present disclosure. FIG. 3A shows a structure of a gas-responsive neuron module, mimicking olfactory neurons according to an embodiment of the present disclosure, and FIG. 3B shows a cross-sectional view of a single transistor neuron formed in a neuron module according to an embodiment of the present disclosure.

Referring to FIG. 2, the olfactory receptor senses gas components and converts the gas components into the electrical signal. The converted signal is transmitted to the olfactory bulb where a mitral cell and an interneuron are located via a glomeruli. The signal preprocessing is performed in the olfactory bulb, and the preprocessed signal is transmitted to the olfactory cortex of a brain to identify the smell.

Referring to FIG. 3A, a gas-responsive neuron module 100 according to an embodiment of the present disclosure is composed of a resistive gas sensor 110 and a single transistor neuron 120.

The resistive gas sensor 110 plays a role of the olfactory receptor that senses the smell and converts the smell into the electrical signal, and a drain 125 of the single transistor neuron 120 plays a role of the mitral cell that outputs a spike signal based on a gas environment. In addition, a gate 127 of the single transistor neuron 120 plays a role of the interneuron that enables more efficient identification by increasing a signal contrast difference via an inhibition function. A metal wire that connects the resistive gas sensor 110 and the single transistor neuron 120 to each other plays a role of the glomeruli that transmits the signal of the olfactory receptor to the mitral cell.

The resistive gas sensor 110 may be formed as one of a semiconducting metal oxide (SMO) gas sensor, a carbon nanotube (CNT)-based gas sensor, and a polymer-based gas sensor. In this regard, the SMO gas sensor may be formed of one of tin oxide ($SnO_2$), tungsten oxide ($WO_3$), zinc oxide (ZnO), indium oxide ($In_2O_3$), titanium oxide ($TiO_2$), copper oxide (CuO), and nickel oxide (NiO). In addition, a heater or a photoactive platform that increases a temperature may be integrated at the same time to improve responsiveness of the SMO gas sensor. The carbon nanotube-based gas sensor may be formed as one of a single-walled carbon nanotube and a multi-walled carbon nanotube. In addition, the polymer-based gas sensor may be formed of one of polypyrrole, polyaniline, polythiophene, polyacetylene, and a conductive polymer.

As shown in FIG. 3B, the single transistor neuron 120 includes a semiconductor substrate 121, a hole barrier material layer 122 formed on top of the semiconductor substrate 121, a floating body layer 123 formed on top of the hole barrier material layer 122, a source 124 and the drain 125 formed on left and right sides or on top of and beneath the floating body layer 123, a gate insulating film 126 formed on top of the floating body layer 123, and the gate 127 formed on top of the gate insulating film 126.

The substrate 121 may represent a single crystal semiconductor substrate, and may be formed of one of silicon (Si), silicon germanium (SiGe), strained silicon (strained Si), strained silicon germanium (strained SiGe), a silicon-on-insulator (SOI), silicon carbide (SiC), and a group 3-5 compound semiconductor. The substrate 121 may act as a back-gate that applies a bias voltage, and the hole barrier material layer 122 and the floating body layer 123 are sequentially positioned on the substrate 121.

The hole barrier material layer 122 may be formed on the substrate 121, may contain a hole barrier material or an electron barrier material, and may be formed of one of buried oxide, a buried n-well in a case of being a p-type body, a buried p-well in a case of being an n-type body, buried SiC, and buried SiGe.

The floating body layer 123 may be formed on the hole barrier material layer 122 and may be formed of one of silicon, germanium, silicon germanium, and a group 3-5 compound semiconductor. Holes generated by impact ionization are accumulated in the floating body layer 123, enabling a spiking operation of the neuron. The floating body layer 123 may represent a structure of one of a planar floating body layer, a vertical floating body layer, a fin-type floating body layer having a protruding channel, and a nanowire-type or nanosheet-type floating body layer.

According to an embodiment, the floating body layer 123 may be formed in a horizontal direction or a vertical direction on the semiconductor substrate 121. When the floating body layer 123 is formed in the horizontal direction, the single transistor neuron 120 may represent a horizontal transistor structure, and when the floating body layer 123 is formed in the vertical direction, the single transistor neuron 120 may represent a vertical transistor structure.

According to another embodiment, the single transistor neuron 120 may further include a lower substrate (not shown) formed under the floating body layer 123, and the lower substrate may be operable as the back-gate.

The source 124 and the drain 125 may be formed on the left and right sides of the floating body layer 123 in the case of the horizontal transistor, may be formed on top of and beneath the floating body layer 123 in the case of the vertical transistor, and may be formed of one of n-type silicon, p-type silicon, and metal silicide. In this regard, the source 124 and the drain 125 may be of a different type from the floating body layer 123. For example, when the source 124 and the drain 125 are of a p-type, the floating body layer 123 may be of an n-type, and when the source 124 and the drain 125 are of the n-type, the floating body layer 123 may be of the p-type.

The source 124 and the drain 125 may be formed via one of diffusion, solid-phase diffusion, epitaxial growth and selective epitaxial growth, ion implantation, and subsequent heat treatment.

In addition, the source 124 and the drain 125 may be the metal silicide formed of one of erbium (Er), ytterbium (Yb), samarium (Sm), yttrium (Y), gadolinium (Gd), terbium (Tb), cerium (Ce), platinum (Pt), lead (Pb), iridium (Ir), nickel (Ni), titanium (Ti), tungsten (W), and cobalt (Co). In this case, the single transistor neuron 120 may be a Schottky barrier transistor. In addition, dopant segregation may be used for improved bonding, and the single transistor neuron 120 may be a dopant segregation Schottky barrier transistor.

The gate insulating film 126 formed on top of the floating body layer 123 insulates the floating body layer 123 and the gate 127 from each other. The gate insulating film 126 may be formed of one of silicon oxide, a nitride film, aluminum oxide, hafnium oxide, hafnium oxynitride, zinc oxide, zirconium oxide, and zirconium hafnium oxide (HZO), or a combination thereof. In addition, the gate insulating film 126 may include a charge storage layer such as poly-silicon, amorphous silicon, metal oxide, silicon nitride, silicon oxynitride, a silicon nano-crystal, and a metal oxide nano-crystal.

The gate 127 may be formed on top of the gate insulating film 126 and may be formed of one of n-type polysilicon, p-type polysilicon, and metal. The corresponding metal may be aluminum (Al), molybdenum (Mo), magnesium (Mg), chromium (Cr), palladium (Pd), platinum (Pt), nickel (Ni), titanium (Ti), gold (Au), tantalum (Ta), tungsten (W), silver (Ag), tin (Sn), titanium nitride (TiN), tantalum nitride (TaN), or a combination thereof.

The single transistor neuron 120 may have a gate-all-around (GAA) transistor structure in which the floating body layer 123 has the nanowire structure or the nanosheet structure and the gate insulating film 126 and the gate 127 surround the floating body layer 123. The channel is isolated by vertically arranged n+ source and n+ drain in the case of the p-type body and by vertically arranged p+ source and p+ drain in the case of the n-type body, so that the holes generated by the impact ionization may be trapped without the hole barrier material, and thus the hole barrier material may not be present.

When the gate 127 represents the gate-all-around (GAA) structure of surrounding an entirety of the floating body layer 123, the hole barrier material layer 122 may not be required. In addition, the gate 127 may represent a multiple-gate structure of a double-gate, a tri-gate, and an omega-gate.

The neuron module 100 including the resistive gas sensor 110 and the single transistor neuron 120 according to an embodiment of the present disclosure may apply an appropriate voltage to the gate 127 to inhibit spiking of the gas-responsive neuron module and may increase the signal contrast difference to enable the more efficient gas identification.

The resistive gas sensor 110 and the single transistor neuron 120 may be manufactured on different substrates and connected to each other by wire bonding, or may be manufactured on the same substrate and connected to each other by interconnect metal.

When the gas identification is performed using the gas-responsive neuron module 100 according to an embodiment of the present disclosure, because the conversion circuit for the signal transmission between the sensor array and the processor and the von Neumann-based computer for the pattern recognition of the existing electronic nose may be removed, the hardware area and the energy consumption of the electronic nose may be reduced, so that high-integration and low-power neuromorphic electronic nose and gas sensing system for the portable gas monitoring device for the Internet of Things (IoT) may be implemented.

The neuromorphic electronic nose and the gas sensing system according to an embodiment of the present disclosure may include one or more additional components of a synaptic element, a resistor, a capacitor, and a transistor based on a system to be applied in addition to the gas-responsive neuron module.

In addition, the neuromorphic electronic nose and the gas sensing system according to an embodiment of the present disclosure may be applied to air pollution-related indoor/outdoor air quality monitoring, early diagnosis of a respiratory-related disease, food/beverage quality monitoring and identification, toxic gas detection at an industrial site, and the like.

FIGS. 4A, 4B, 4C and 4D, FIGS. 5A, 5B, 5C and 5D show graphs of electrical measurement results based on a gas environment of a gas-responsive neuron module actually manufactured according to an embodiment of the present disclosure.

As the resistive gas sensor, tin oxide ($SnO_2$) and tungsten oxide ($WO_3$), which are the SMO gas sensors, were used, and as the single transistor neuron, the horizontal transistor manufactured on an SOI substrate was used. 7.5 V was applied as an operating voltage ($V_{DD}$) of the gas sensor, and a heater power of 12.9 mW was applied as a MEMS-based heater was integrated to improve the responsiveness of the gas sensor. In addition, 0 V was applied to the gate and the source of the single transistor neuron. An output voltage ($V_{out}$) was measured at the drain of the single transistor neuron. Ammonia ($NH_3$), carbon monoxide (CO), nitrogen dioxide ($NO_2$), and acetone were used as input gases.

Figure 4A:
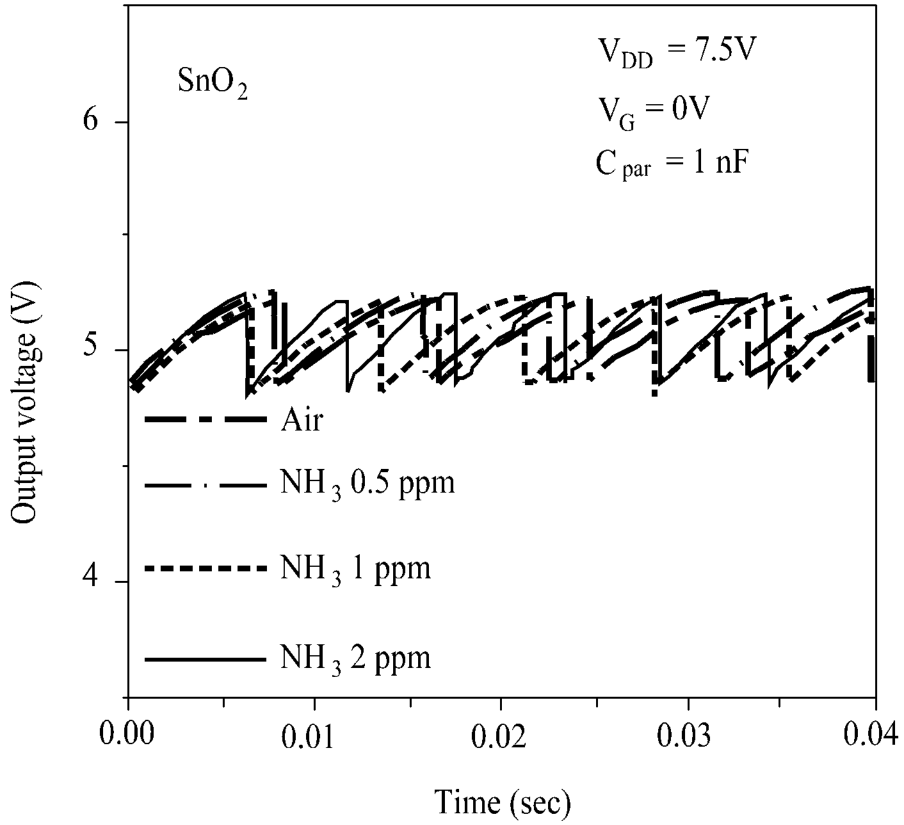
FIGS. 4A, 4B, 4C, and 4D, FIGS. 5A, 5B, 5C, and 5D show graphs of electrical measurement results based on a gas environment of a gas-responsive neuron module actually manufactured according to an embodiment of the present disclosure.
Figure 4B:
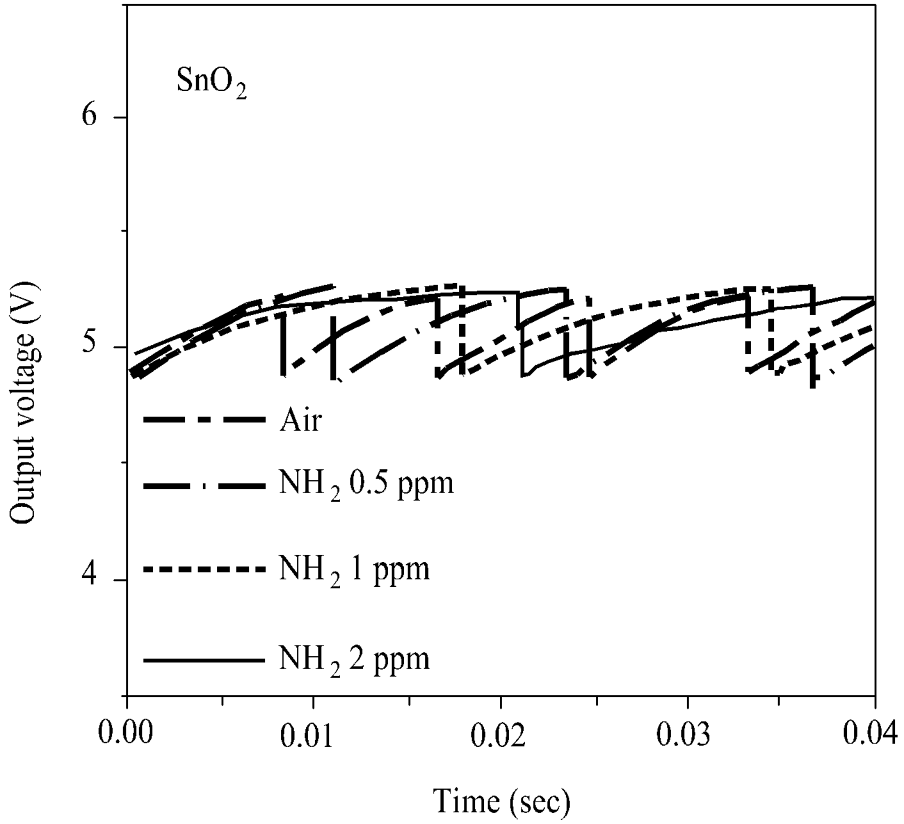
Figure 4C:
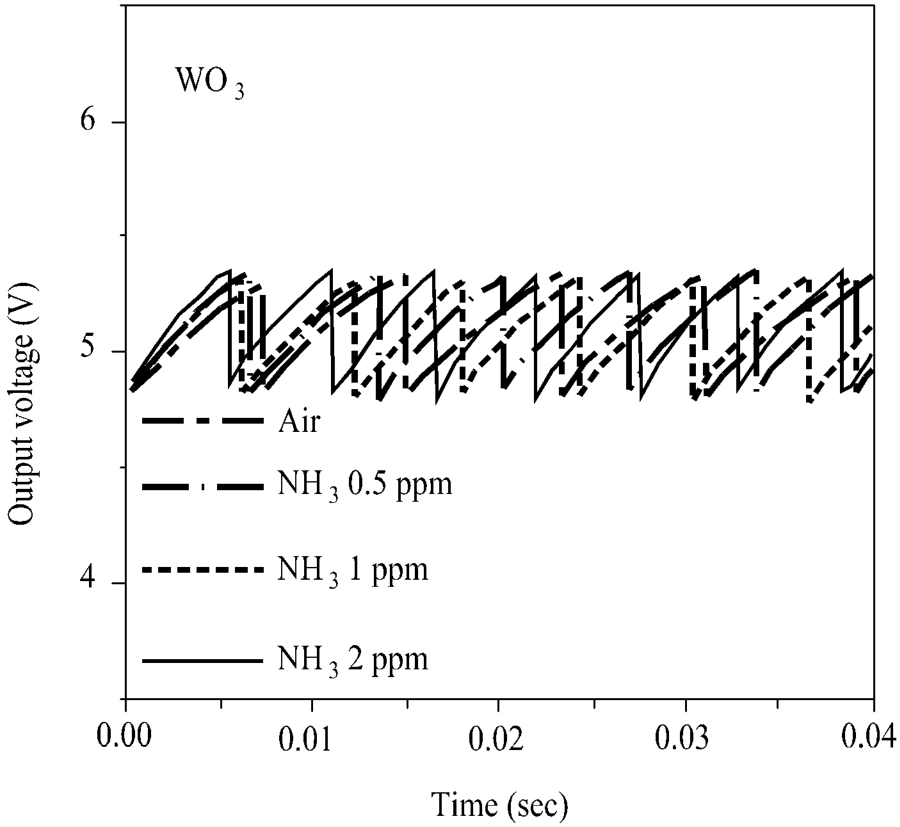
Figure 4D:
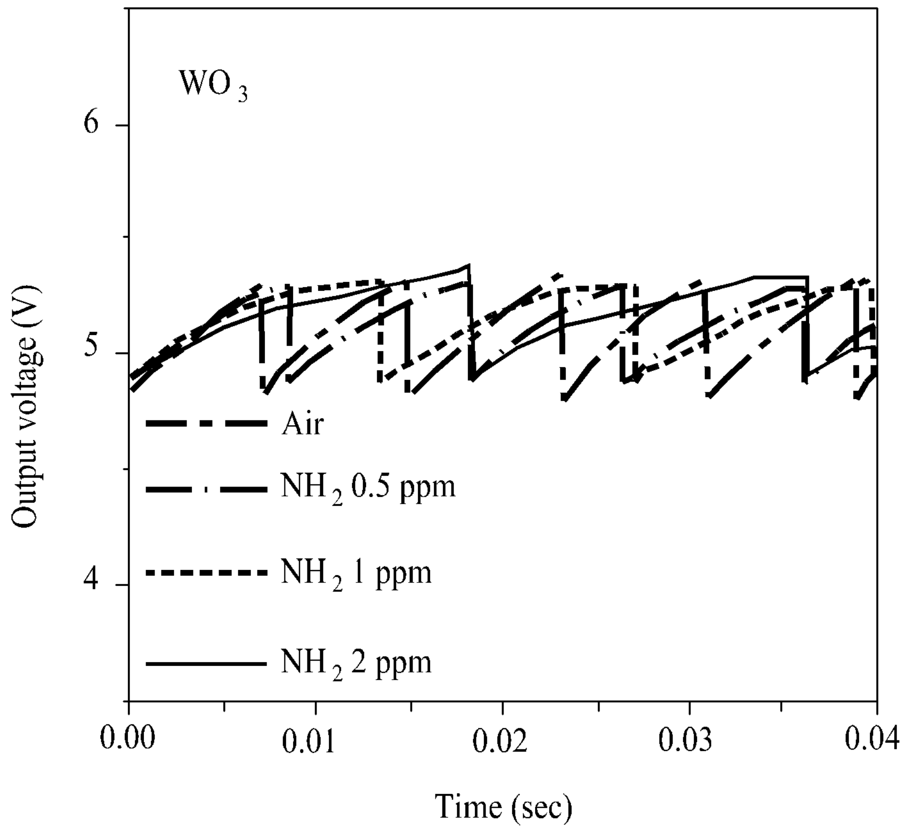
Figure 5A:
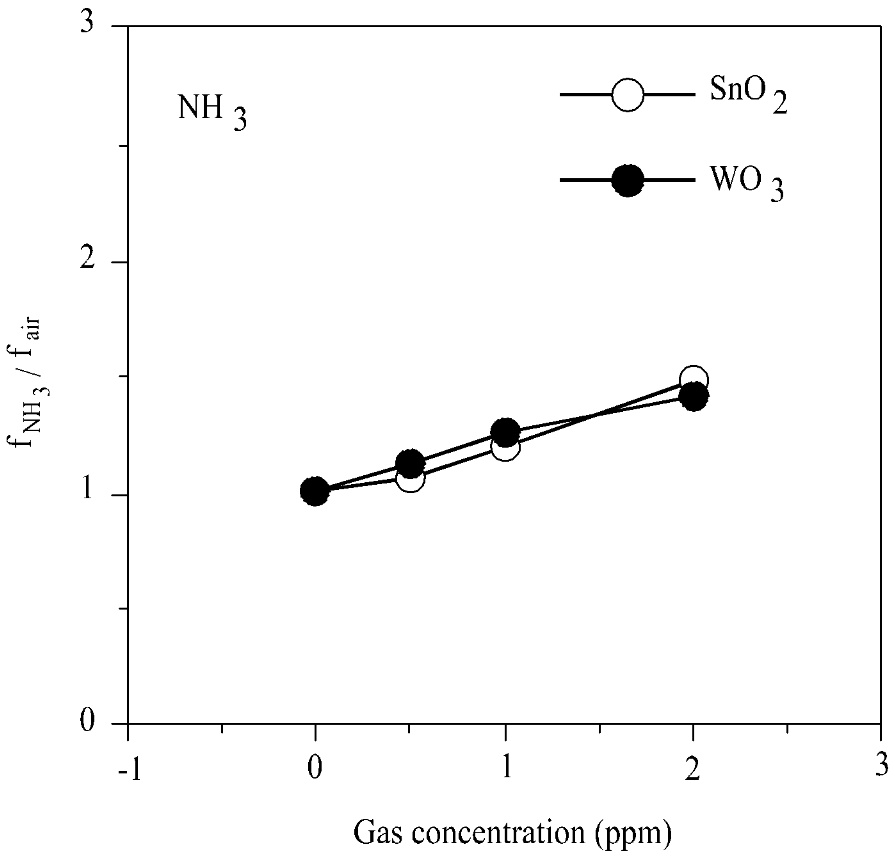
Figure 5B:
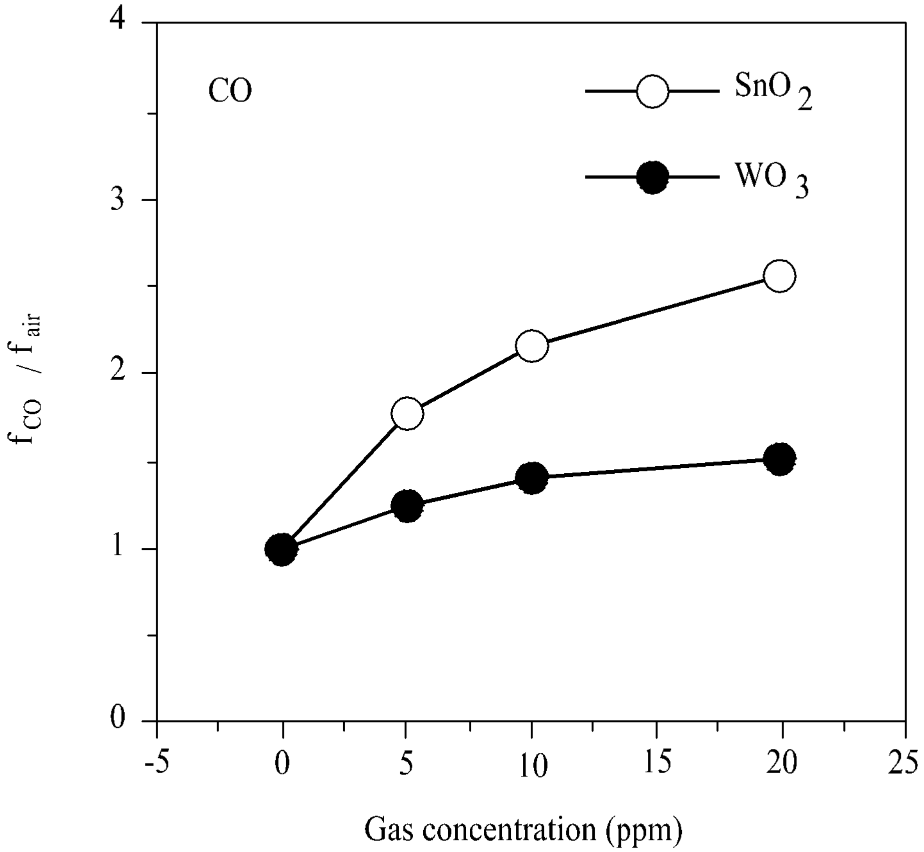
Figure 5C:
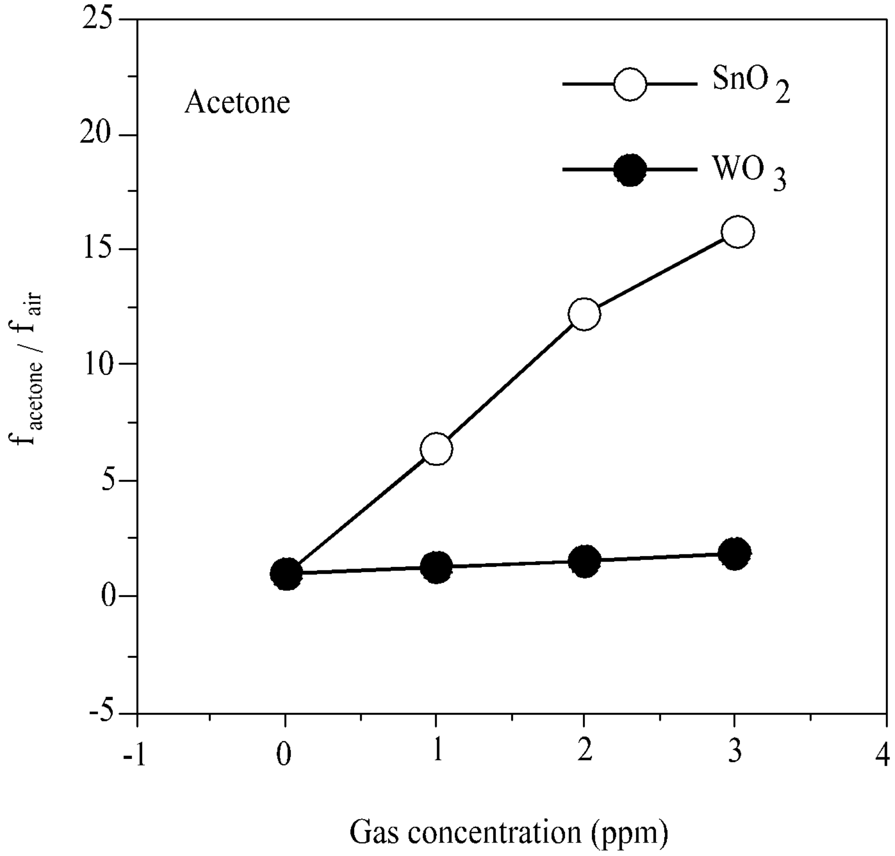
Figure 5D:
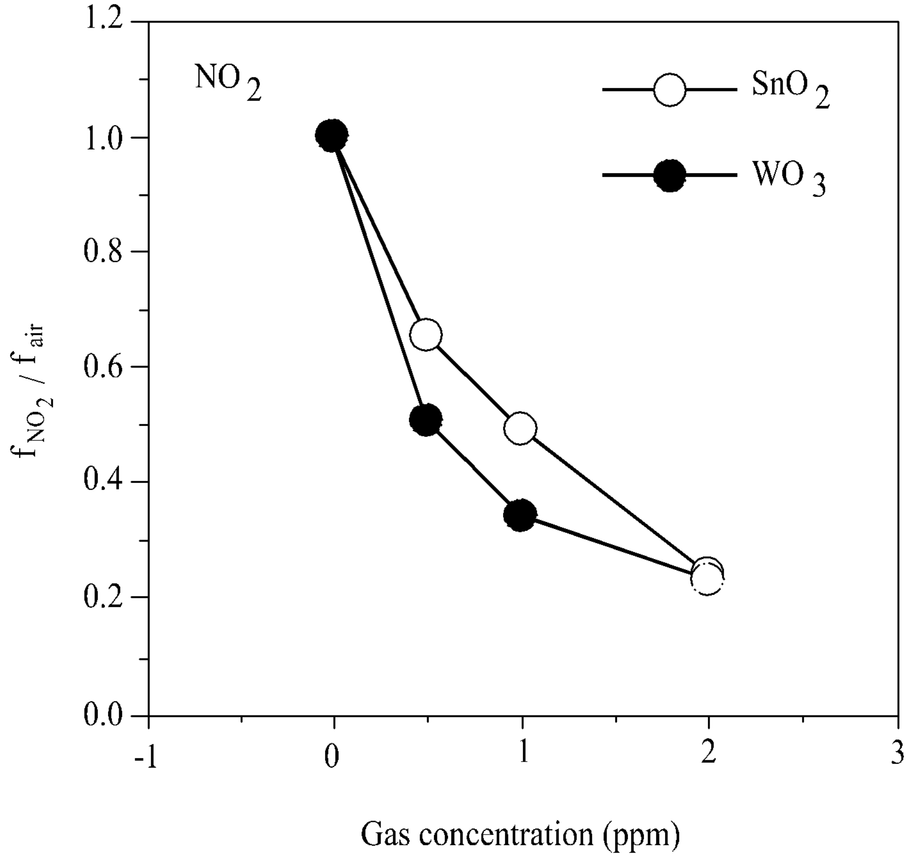

Referring to FIGS. 4A, 4B, 4C and 4D, graphs in FIGS. 4A and 4B show output voltages over time in ammonia ($NH_3$) and nitrogen dioxide ($NO_2$) environments of a gas-responsive neuron module composed of the tin oxide ($SnO_2$) gas sensor and the single transistor neuron, respectively, and graphs in FIGS. 4C and 4D show output voltages over time in the ammonia ($NH_3$) and nitrogen dioxide ($NO_2$) environments of a gas-responsive neuron module composed of the tungsten oxide ($WO_3$) gas sensor and the single transistor neuron, respectively.

It may be seen that, in both the gas-responsive neuron module composed of the $SnO_2$ gas sensor and the single transistor neuron and the gas-responsive neuron module composed of the $WO_3$ gas sensor and the single transistor neuron, a spiking frequency increases as a concentration of $NH_3$ increases, whereas the spiking frequency decreases as a concentration of $NO_2$ increases. This is because a resistance of the gas sensor is lowered and thus a current input to the single transistor neuron is increased in the $NH_3$ environment, and the resistance of the gas sensor is increased and thus the current input to the single transistor neuron is reduced in the $NO_2$ environment.

In FIGS. 5A, 5B, 5C and 5D, graphs in FIGS. 5A, 5B, 5C and 5D show change rates ($f_{gas}/f_{air}$) the spiking frequency based on a gas concentration in ammonia ($NH_3$), carbon monoxide (CO), acetone, and nitrogen dioxide ($NO_2$) environments, respectively. It may be seen that, in both the gas-responsive neuron module composed of the $SnO_2$ gas sensor and the single transistor neuron and the gas-responsive neuron module composed of the $WO_3$ gas sensor and the single transistor neuron, the spiking frequency increases as concentrations of $NH_3$, CO, and acetone increase, whereas the spiking frequency decreases as the concentration of $NO_2$ increases. As a result, the gas-responsive neuron module whose spiking frequency changes based on the gas environment was implemented.

Figure 6:
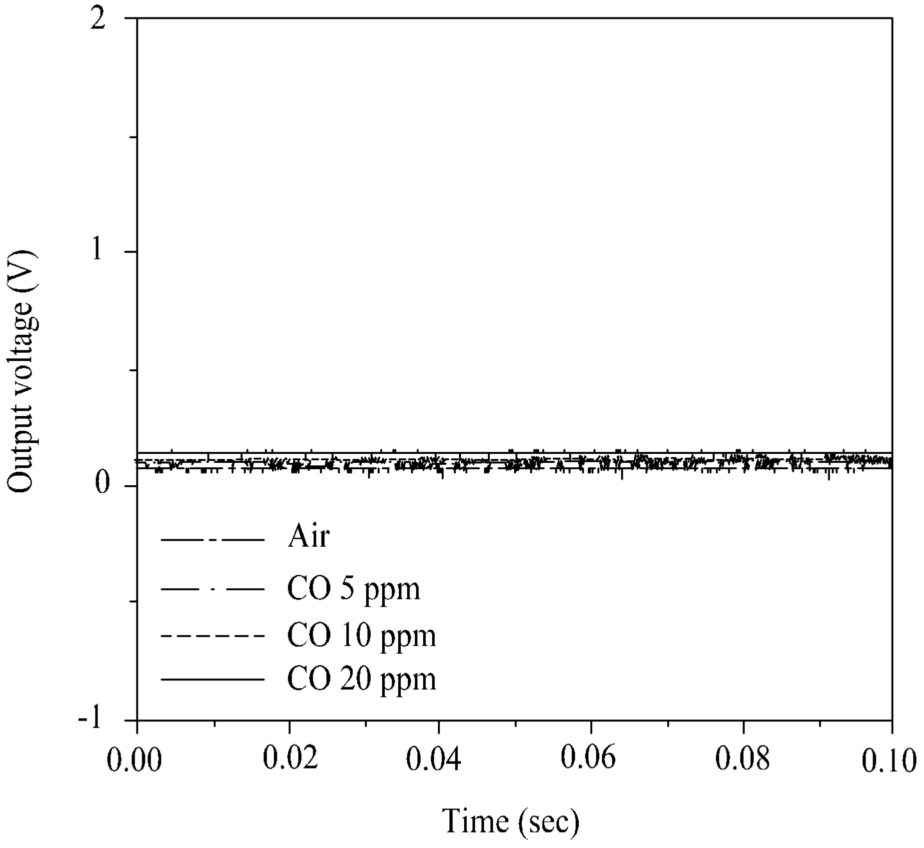
FIG. 6 shows a graph of electrical measurement results implementing an inhibition function of a gas-responsive neuron module manufactured according to an embodiment of the present disclosure.

FIG. 6 shows a graph of electrical measurement results implementing an inhibition function of a gas-responsive neuron module manufactured according to an embodiment of the present disclosure.

To implement the inhibition function, 2 V was applied to the gate of the single transistor neuron. As a result, as shown in FIG. 6, it may be seen that the spiking is suppressed regardless of a concentration of the input CO gas. Such inhibition function makes a signal contrast to enable the more efficient gas identification.

Figure 7A:
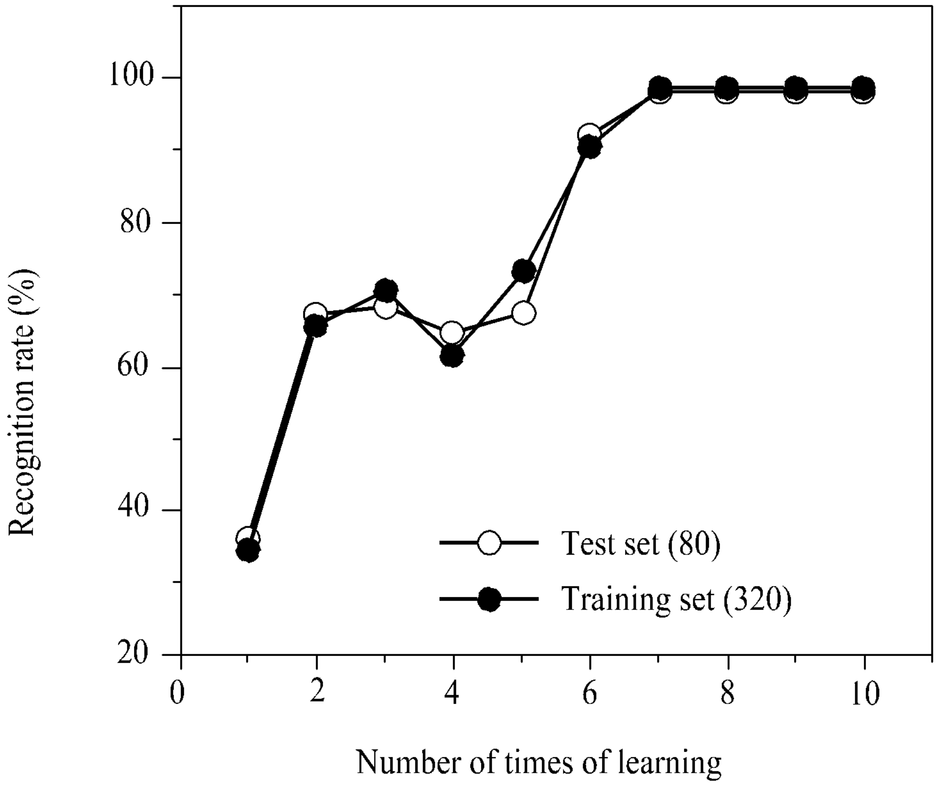
FIGS. 7A and 7B show graphs of results of simulation for identifying four kinds of gases using a gas-responsive neuron module manufactured according to an embodiment of the present disclosure.
Figure 7B:
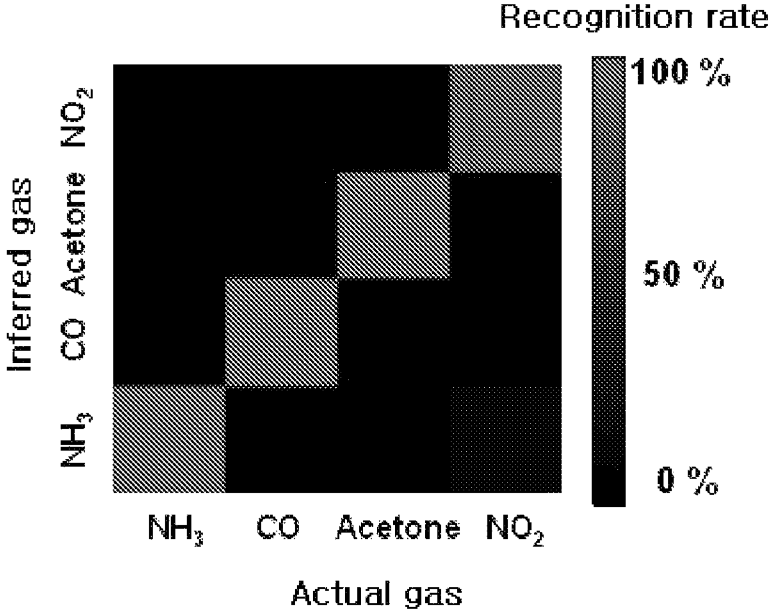

FIGS. 7A and 7B show graphs of results of simulation for identifying four kinds of gases using a gas-responsive neuron module manufactured according to an embodiment of the present disclosure.

To identify the gases, a neural network composed of two hidden layers was constructed, and each hidden layer was composed of 100 neurons. An input layer was composed of two neurons, and the spiking frequency of the gas-responsive neuron module actually measured in FIGS. 4 and 5 was reflected. In addition, an output layer was composed of 4 neurons representing the respective gases. To detect N kinds of gases, N output layer neurons are required, and the number of hidden layer neurons needs to be increased for more complex pattern recognition.

FIG. 7A is a graph showing a recognition rate based on the number of times of learning. It may be seen that the recognition rate increases as the number of times of learning increases. A recognition rate of 98.25% is exhibited after 7 times of learning.

FIG. 7B is a graph showing recognition rates of inferred gases based on actual gases in a form of a matrix. It may be seen that the four kinds of gases may be identified with a recognition rate close to 100%.

Figure 8:
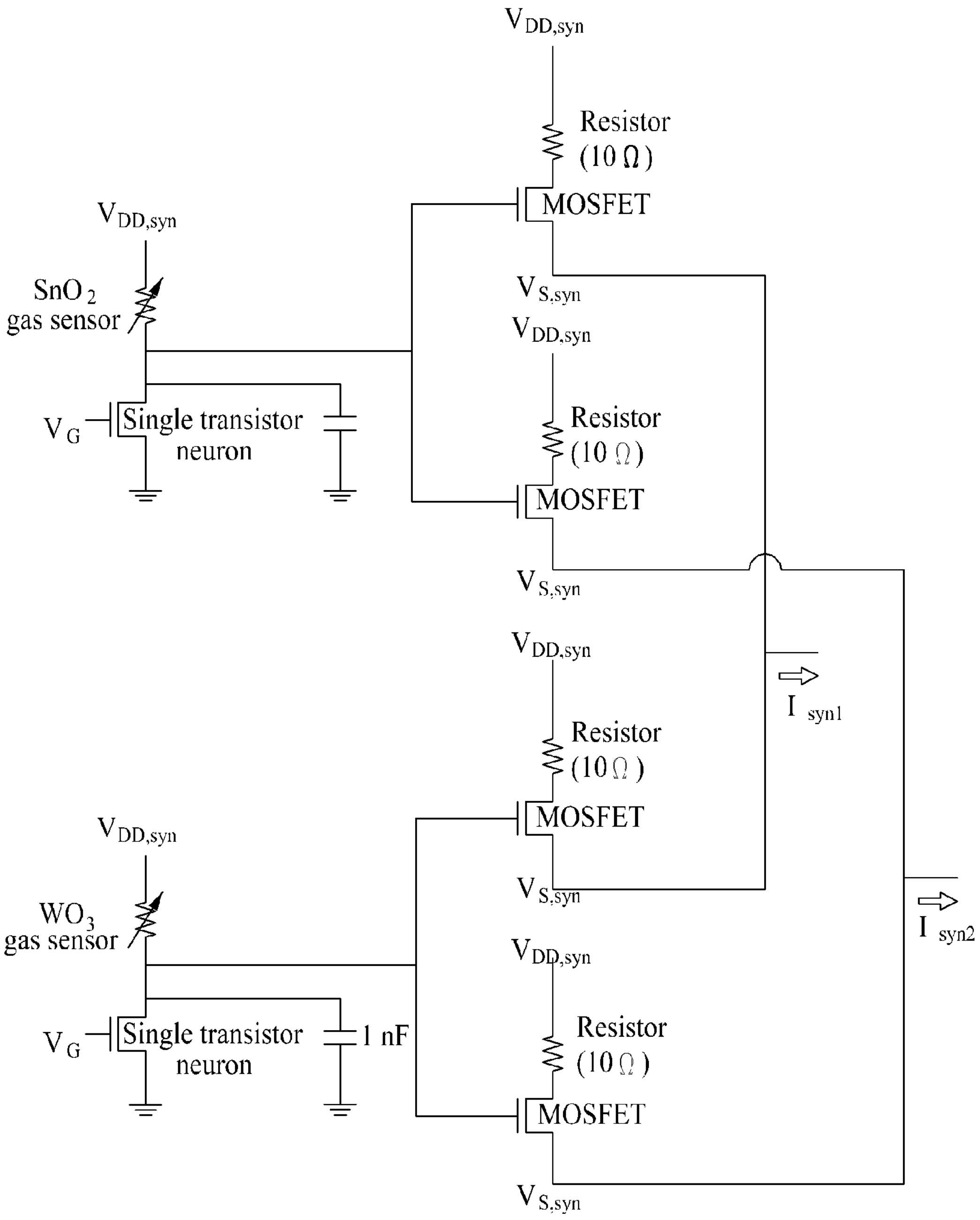
FIGS. 8, 9A and 9B show a circuit diagram of hardware constructed to identify two kinds of wine using a gas-responsive neuron module manufactured according to an embodiment of the present disclosure and electrical measurement result graphs.
Figure 9A:
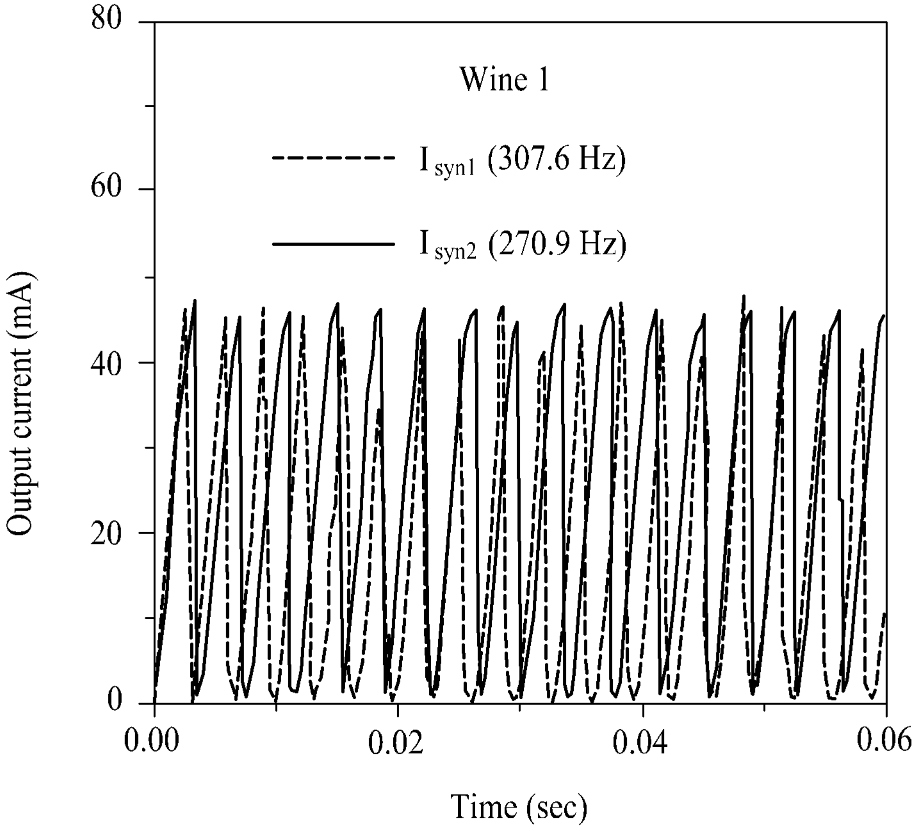
Figure 9B:
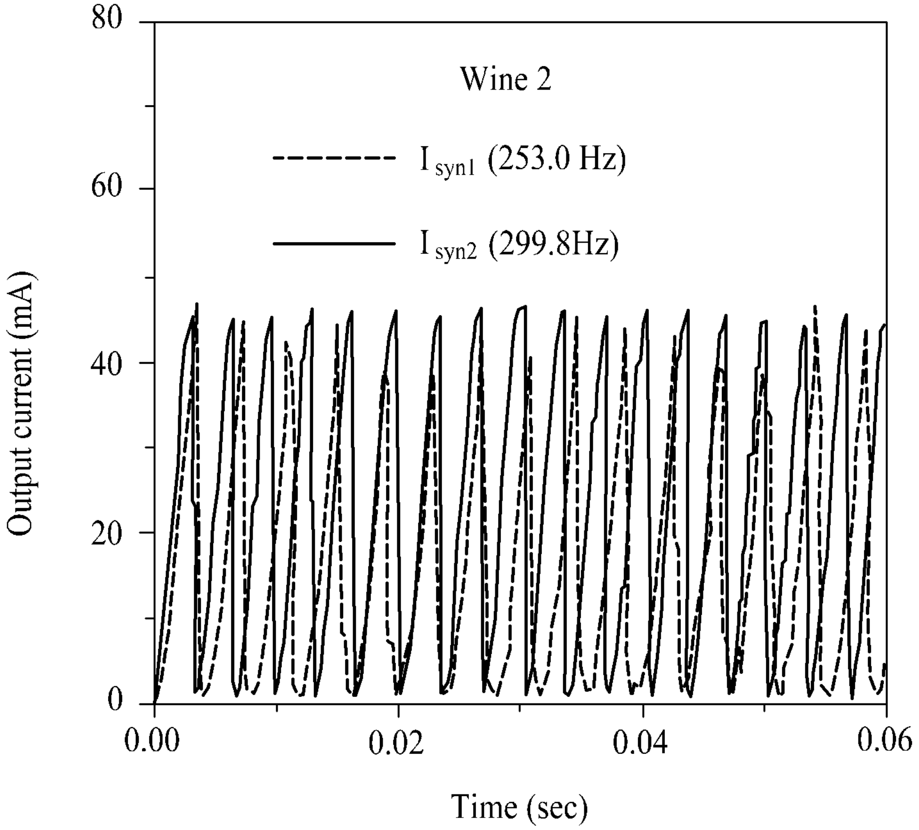

FIGS. 8, 9A and 9B show a circuit diagram of hardware constructed to identify two kinds of wine using a gas-responsive neuron module manufactured according to an embodiment of the present disclosure and electrical measurement result graphs.

Referring to FIG. 8, the output voltages from the gas-responsive neuron module composed of the tin oxide ($SnO_2$) gas sensor and the single transistor neuron and the gas-responsive neuron module composed of the tungsten oxide ($WO_3$) gas sensor and the single transistor neuron are transmitted to synapses of a 1T1R structure composed of one MOSFET (transistor) and one resistor. In this regard, a weight of the synapse may be adjusted via strengthening/weakening based on a degree of learning. The two kinds of wine may be distinguished from each other by comparing a spiking frequency of a current ($I_{syn1}$) output from one of synapses connected to the gas-responsive neuron module composed of the $SnO_2$ gas sensor and the single transistor neuron and one of synapses connected to the gas-responsive neuron module composed of the $WO_3$ gas sensor and the single transistor neuron with a spiking frequency of a current ($I_{syn2}$) output from another of the synapses connected to the gas-responsive neuron module composed of the $SnO_2$ gas sensor and the single transistor neuron and another of the synapses connected to the gas-responsive neuron module composed of the $WO_3$ gas sensor and the single transistor neuron. In one example, the capacitor was connected to the gas-responsive neuron module to adjust a level of the spiking frequency. The weight of the 1T1R synapse is determined by a resistance. A synaptic resistance of a high weight was set to 10Ω, and a synaptic resistance of a low weight was set to 10 kΩ. An operating voltage ($V_{DD,sen}$) of the gas sensor was 7.5 V, a gate voltage ($V_G$) and a source voltage of the single transistor neuron were 0 V, and an operating voltage ($V_{DD,syn}$) and a source voltage ($V_{S,syn}$) were 5 V and 3 V, respectively.

Referring to FIGS. 9A and 9B, it may be seen that the spiking frequency of $I_{syn1}$ is higher when a first wine gas in FIG. 9A is input, and the spiking frequency of $I_{syn2}$ is higher when a second wine gas in FIG. 9B is input. Therefore, the food/beverage identification other than the gas identification may be performed using the gas-responsive neuron module.

When the gas identification is performed using the gas-responsive neuron module, because the conversion circuit for the signal transmission between the sensor array and the processor and the von Neumann-based computer for the pattern recognition of the existing electronic nose may be removed, the hardware area and the energy consumption of the electronic nose may be reduced, so that the high-integration and low-power neuromorphic electronic nose for the portable gas monitoring device for the Internet of Things (IoT) may be implemented.

The system or the device described above may be implemented with a hardware component, a software component, and/or a combination of the hardware component and the software component. For example, the device and the component described in the embodiments may be implemented using at least one general purpose computer or a special purpose computer, such as, for example, a processor, a controller, an arithmetic logic unit (ALU), a digital signal processor, a microcomputer, a field programmable gate array (FPGA), a programmable logic unit (PLU), a microprocessor, or any other device capable of executing and responding to instructions. The processing device may execute an operating system (OS) and at least one software application running on the operating system. The processing device may also access, store, manipulate, process, and generate data in response to the execution of the software. For convenience of understanding, there is a case in which one processing device is described as being used, but a person of ordinary skill in the art will recognize that the processing device may include a plurality of processing elements and/or a plurality of types of processing elements. For example, the processing device may include a plurality of processors or one processor and one controller. Other processing configurations, such as parallel processors, are also possible.

The software may include a computer program, a code, an instruction, or a combination of one or more thereof, and may construct the processing device or independently or collectively instruct the processing device to operate as desired. The software and/or the data may be permanently or temporarily embodied in any type of machine, a component, a physical device, virtual equipment, a computer storage medium or device, or a transmitted signal wave to be interpreted by or to provide the instruction or the data to the processing device. The software may be distributed over a networked computer system, and stored or executed in a distributed manner. The software and the data may be stored in at least one computer-readable recording medium.

The methods according to the embodiments may be implemented in a form of program instructions that may be executed through various computer means, and recorded in computer-readable media. The computer-readable media may also include, alone or in combination with the program instructions, data files, data structures, and the like. The program instructions recorded on the medium may be specially designed and configured for the embodiments, or may be known and available to those skilled in the art of computer software. Examples of computer-readable recording media include magnetic media such as a hard disk, a floppy disk, and a magnetic tape, optical media such as a CD ROM disk and a DVD, magneto-optical media such as a floptical disk, and hardware devices that are specially configured to store and perform program instructions, such as a read-only memory (ROM), a random access memory (RAM), a flash memory, and the like. Examples of the program instructions include both a machine code, such as produced by a compiler, and a higher level code that may be executed by the computer using an interpreter and the like. The described hardware devices may be configured to act as one or more software modules to perform the operations of the embodiments, or vice versa.

As described above, although the embodiments have been described with the limited embodiments and drawings, various modifications and variations are possible from the above description by those skilled in the art. For example, suitable results may be achieved even when the described technologies are performed in an order different from that of the described method, and/or when components in a described system, an architecture, a device, or a circuit are coupled or combined in a manner different from that of the described method and/or replaced or supplemented by other components or equivalents thereof.

Therefore, other implementations, other embodiments, and equivalents to the claims also fall within the scope of the following claims.

According to an embodiment of the present disclosure, because the conversion circuit for the signal transmission between the sensor array and the processor and the von Neumann-based computer for the pattern recognition of the existing electronic nose may be removed using the gas-responsive neuron module, the hardware area and the energy consumption of the electronic nose may be minimized. Therefore, the high-integration and low-power gas sensing system for the portable gas monitoring device for the Internet of Things (IoT) may be implemented.

However, effects of the present disclosure are not limited to the above effects, and may be variously extended within a range that does not deviate from the technical spirit and scope of the present disclosure.

While the present disclosure has been described with reference to exemplary embodiments, it will be apparent to those skilled in the art that various changes and modifications may be made without departing from the spirit and scope of the present disclosure. Therefore, it should be understood that the above embodiments are not limiting, but illustrative.

What is claimed is:

1. A gas-responsive neuron module comprising:

a resistive gas sensor for sensing gaseous molecules and converting the sensed gaseous molecules into an electrical signal; and a single transistor neuron composed of a source, a drain, and a gate;

wherein the single transistor neuron includes:

a semiconductor substrate;

a hole barrier material layer formed on top of the semiconductor substrate;

a floating body layer formed on top of the hole barrier material layer; wherein the source and the drain are formed on left and right sides or on top of and beneath the floating body layer;

a gate insulating film formed on top of the floating body layer, the gate formed on top of the gate insulating film;

wherein the electrical signal from the gas responsive sensor is electrically coupled with the drain; and wherein the single transistor neuron is configured to functions as a spiking neural network that produces a series of output voltage spikes at the drain, and wherein a frequency of the voltage spikes is determined by said electrical signal.

2. The gas-responsive neuron module of claim 1, wherein the resistive gas sensor is formed as one of a semiconducting metal oxide (SMO) gas sensor, a carbon nanotube (CNT)-based gas sensor, and a polymer-based gas sensor.

3. The gas-responsive neuron module of claim 2, wherein the SMO gas sensor is formed of one of tin oxide ($SnO_2$), tungsten oxide ($WO_3$), zinc oxide (ZnO), indium oxide ($In_2O_3$), titanium oxide ($TiO_2$), copper oxide (CuO), and nickel oxide (NiO).

4. The gas-responsive neuron module of claim 2, wherein the resistive gas sensor is simultaneously integrated with a heater or a photoactive platform for increasing a temperature to improve responsiveness of the SMO gas sensor.

5. The gas-responsive neuron module of claim 2, wherein the carbon nanotube-based gas sensor is formed as a single-walled carbon nanotube or a multi-walled carbon nanotube, or wherein the polymer-based gas sensor is formed of one of polypyrrole, polyaniline, polythiophene, polyacetylene, and a conductive polymer.

6. The gas-responsive neuron module of claim 1, wherein the gate serves as a biological interneuron by performing an inhibition function, wherein the drain serves as a biological mitral cell by performing a function of outputting a spike signal.

7. The gas-responsive neuron module of claim 1, wherein the hole barrier material layer is formed of one of buried oxide, a buried n-well in a case of being a p-type body, a buried p-well in a case of being an n-type body, buried SiC, and buried SiGe.

8. The gas-responsive neuron module of claim 1, wherein holes generated by impact ionization are accumulated in the floating body layer, and the floating body layer is formed of one of silicon, germanium, silicon germanium, and a group 3-5 compound semiconductor.

9. The gas-responsive neuron module of claim 1, wherein the floating body layer is formed in a horizontal direction or a vertical direction on the semiconductor substrate, wherein the single transistor neuron represents a horizontal transistor structure when the floating body layer is formed in the horizontal direction, and the single transistor neuron represents a vertical transistor structure when the floating body layer is formed in the vertical direction.

10. The gas-responsive neuron module of claim 1, wherein the floating body layer includes a lower substrate, wherein the lower substrate is operable as a back-gate.

11. The gas-responsive neuron module of claim 10, wherein the source and the drain formed of n-type silicon or p-type silicon are formed via one of diffusion, solid-phase diffusion, epitaxial growth and selective epitaxial growth, ion implantation, and subsequent heat treatment.

12. The gas-responsive neuron module of claim 1, wherein the source and the drain are formed on the left and right sides of the floating body layer in a case of a horizontal transistor, are formed on top of and beneath the floating body layer in a case of a vertical transistor, and are formed of one of n-type silicon, p-type silicon, and metal silicide.

13. The gas-responsive neuron module of claim 1, wherein the gate represents a gate-all-around (GAA) structure of surrounding an entirety of the floating body layer.

14. The gas-responsive neuron module of claim 13, wherein the gate represents a multiple-gate structure of a double-gate, a tri-gate, and an omega-gate.

15. The gas-responsive neuron module of claim 1, wherein the neuron module applies an appropriate voltage to the gate to inhibit spiking for enabling gas identification.

16. The gas-responsive neuron module of claim 1, wherein the neuron module includes the resistive gas sensor and the single transistor neuron manufactured on different substrates and connected to each other by wire bonding, or the resistive gas sensor and the single transistor neuron manufactured on the same substrate and connected to each other by interconnect metal.

17. The gas-responsive neuron module of claim 1, wherein the electrical coupling of the electrical output of the resistive gas sensor and the drain takes place via a metal wire or an interconnect.

* * * * *